United States Patent [19]

Dorgan et al.

[11] Patent Number: 4,866,056
[45] Date of Patent: * Sep. 12, 1989

[54] BENZAZEPINES AND METHODS THEREFOR

[75] Inventors: Roderick J. Dorgan, Outwood; Richard L. Elliott, Leatherhead, both of England

[73] Assignee: Beecham Group, p.l.c., United Kingdom

[*] Notice: The portion of the term of this patent subsequent to Apr. 28, 2004 has been disclaimed.

[21] Appl. No.: 908,379

[22] Filed: Sep. 17, 1986

Related U.S. Application Data

[63] Continuation of Ser. No. 630,524, Jul. 13, 1984, Pat. No. 4,661,489.

[51] Int. Cl.⁴ .................. A61K 31/55; C07D 223/00; C07D 267/08
[52] U.S. Cl. ................... 514/211; 514/214; 540/578; 540/579
[58] Field of Search ............ 540/547, 579, 578, 559; 514/211, 214

[56] References Cited

U.S. PATENT DOCUMENTS 4,581,172  4/1986  Kaiser et al. .................. 540/579 X
4,661,489  4/1987  Dorgan et al. ................. 514/211

Primary Examiner—Mukund J. Shah
Assistant Examiner—Miriam Sohn
Attorney, Agent, or Firm—Hopgood, Calimafde, Kalil, Blaustein & Judlowe

[57] ABSTRACT

A compound of formula (I):

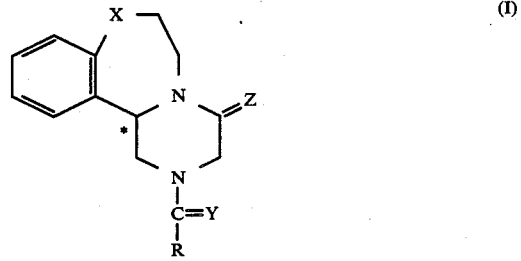

in which R is optionally substituted phenyl; $C_{3-8}$ cycloalkyl; $C_{5-8}$ cycloalkenyl; $C_{1-8}$ alkyl which may be straight or branched; $C_{2-8}$ alkenyl which may be straight or branched; 5- or 6-membered heterocyclyl; or optionally substituted phenyl $C_{1-4}$ alkyl, each of Y and Z, which may be the same or different, is oxygen or sulphur; and X is —$CH_2$— or oxygen, a process for the preparation of such compounds and their use in human and veterinary medicine.

3 Claims, No Drawings

BENZAZEPINES AND METHODS THEREFOR

This is a continuation application of copending U.S. patent application Ser. No. 630,524, filed July 13, 1984, and now U.S. Pat. No. 4,661,489.

The present invention relates to novel benzazepine and benzoxazepine derivatives having anthelmintic activity, to pharmaceutical formulations containing them and to their use in human or veterinary medicine.

The compound praziquantel, which is 2-cyclohexylcarbonyl[1,2,3,6,7,11b]hexahydro-4H-pyrazino[2,1-a]isoquionolin-4-one, is a known compound having anthelmintic activity. Praziquantel has the structure (A)

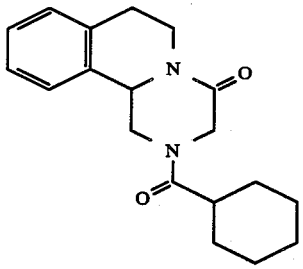
(A)

We have now found a group of compounds having some of the structural features of praziquantel, but also having structural differences, which have useful anthelmintic activity, particularly against tapeworm. According to the present invention there is provided a compound of formula (I):

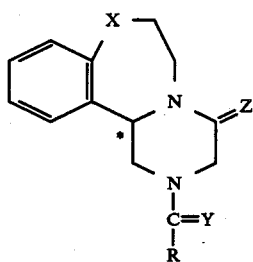
(I)

in which R is optionally substituted phenyl; $C_{3-8}$ cycloalkyl; $C_{5-8}$ cycloalkenyl; $C_{1-8}$ alkyl which may be straight or branched; $C_{2-8}$ alkenyl which may be straight or branched; 5- or 6-membered heterocyclyl; or optionally substituted phenyl $C_{1-4}$ alkyl, each of Y and Z, which may be the same or different, is oxygen or sulphur; and X is —$CH_2$— or oxygen.

Compounds of formula (I) have an asymmetric carbon atom marked by an asterisk in formula (I) and may therefore exist in at least two stereoisomeric forms. The present invention encompasses all isomers of the compounds of formula (I) whether pure or admixed with other isomers in any proportion.

When R is optionally substituted phenyl, it may be substituted with one or more moieties selected from halogen, $C_{1-6}$ alkyl, $C_{1-6}$ alkoxy, nitro, amino, mono-or-di-$C_{1-6}$ alkylamino, and hydroxy. When R is heterocyclyl, it may be a 5 or 6-membered saturated or unsaturated group containing one or more hetero-atoms selected from oxygen, sulphur and nitrogen.

A preferred R group is cyclohexyl.

Compounds of formula (I) may be produced by cyclising a compound of formula (II):

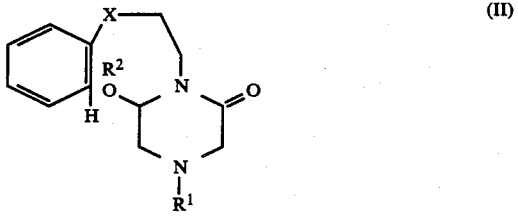
(II)

in which X is as defined in formula (I),
$R^1$ is hydrogen, a protecting group or a group

wherein R and Y are as defined in formula (I) and $R^2$ is $C_{1-3}$ alkyl or hydrogen, and, when $R^1$ is a protecting group, removing the protecting group and replacing it with a group

and, when $R^1$ is hydrogen, replacing it with a group

and optionally thereafter converting the compound of formula (I) thus formed, wherein Z is oxygen, to a compound of formula (I) wherein Z is sulphur, by treatment with a thionation reagent. A preferred thionation reagent is Lawessons reagent. In the above process, replacement of the group

in which Y is sulphur, may be carried out by treatment with a dithioic ester of formula

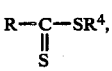

wherein
R is hereinberfore defined and $R^4$ is $C_{1-6}$ alkyl.

As used herein the term 'protecting group' refers to a group which is stable under the cyclisation reaction conditions but which may readily be removed after the cyclisation is complete. A typical example of such a protecting group is benzyl, which may be removed by catalytic hydrogenation, for instance using a palladium catalyst in a suitable solvent.

Examples of $R^2$ are $C_{1-3}$ alkyl and hydrogen, preferably hydrogen.

Compounds of formula (II) may be cyclised by treatment with an acid catalyst, and conveniently an acid such as polyphosphoric acid may be used. The reaction may be conducted at elevated temperature, such as 100° C. or greater, for instance at about 180° C. Alternatively, concentrated sulphuric acid may be used, in which case the reaction is carried out at a lower temperature, for example from 31 10° C. to 40° C.

Compounds of formula (II) wherein $R^2$ is hydrogen may be produced by reducing the corresponding imide of formula (III):

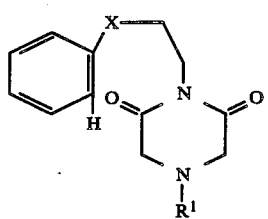

(III)

wherein X, and $R^1$ are as hereinbefore defined. The reduction is effected using a suitable hydride reducing agent, such as sodium borohydride in a suitable solvent such as a lower alkanol, preferably ethanol.

Compounds of formula (II) wherein $R^2$ is alkyl may be produced by conventional methods, such as those outlined in the papers of W. Speckamp et al (for example, see Tetrahedron 31, 1437, 1975).

Compounds of formula (III) may be produced according to Scheme I, using conventional reagents, such as those shown in the scheme.

body, especially for treating helminthiasis and particularly for treating tapeworm infestations, of domestic and farm animals.

The present invention also provides a pharmaceutical or veterinary composition comprising a compound of formula (I) and a pharmaceutically or veterinarily acceptable carrier therefor.

Suitably the compositions consist of sufficient material to provide a dose of from 0.01 to 250 mg of active ingredient per kg of animal body weight per dose, more suitably 0.1 to 50 mg/kg per dose.

The invention also provides a method of treatment or prophylaxis of helminth infections in a human or non-human animal, which comprises the administration to the infected or potentially infected human or animal of an effective non-toxic amount of a compound of formula (I).

In particular aspects this method includes the treatment or prophylaxis of tapeworm infections.

It will be appreciated that, in some cases, it will be advisable to repeat the dosing of the infected or potentially infected human or non-human animal with a compound of formula (I) according to conventional dosage regimes normally used with anthelmintics.

The following Examples illustrate the invention.

Examples XI to X6 and X7 to XII illustrate the preparation of intermediate compounds, while Examples 1 to 35 illustrate the preparation of compounds of the inven- Scheme I

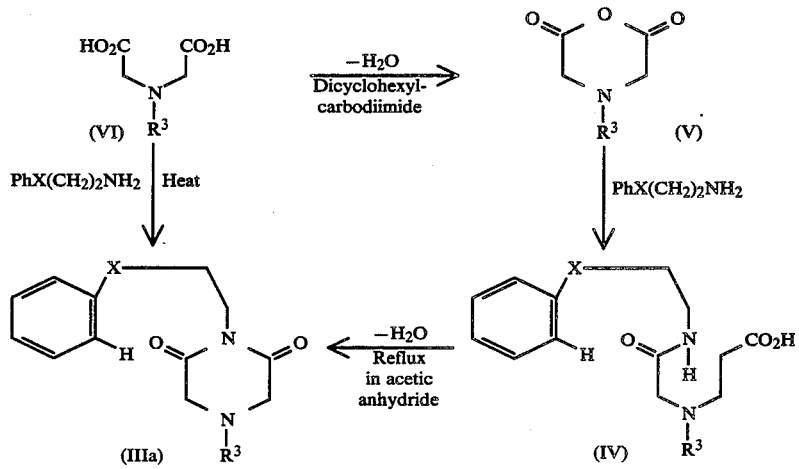

In Scheme I $R^3$ is a protecting group or a group

in which Y is as hereinbefore defined, and X is as hereinbefore defined.

Compounds of formula (III) wherein $R^1$ is hydrogen are produced by removing the protecting group from a compound of formula (IIIa). Further details of the reaction conditions appear in the Examples below.

Compounds of formula (I) have anthelmintic activity especially against tapeworm such as *Taenia taeniaeformis* and *Dipylidium caninum*.

Accordingly the present invention also provides a compound of formula (I), as hereinbefore defined, for use in the treatment of the human or non-human animal tion. Example X7 illustrates the resolution of a compound of the invention.

EXAMPLE 1

2-(Cyclohexylcarbonyl)-4-oxo-1,2,3,4,6,7,8,12b-octahydropyrazino[2,1-a][2]benzazepine Cyclohexanoyl chloride (0.34 g) was added to a solution of 4-oxo-1,2,3,4,6,7,8,12b-octahydropyrazino[2,1a][2]benzazepine (0.5 g) in chloroform (20 ml, ethanol-free) maintained at 0° C. and triethylamine (0.26 g) added. The mixture was maintained at 0° C. for 30 min then at room temperature for 5 h. The solution was washed with, first, dilute hydrochloric acid and secondly with sodium bicarbonate solution. The chloroform solution was dried (MgSO$_4$) and evaporated. The residue was recrystallised from chloroform/40°-60° C.

petroleum ether to give white crystals of the title compound (0.48 g, 64%) m.p. 187°–90° C.

Found: C: 73.2, H: 7.7, N: 8.4%, $C_{20}H_{26}N_2O_2$ requires-C: 73.6, H: 8.0, N: 8.6%

EXAMPLE XI 1-(3-Phenylpropyl)-4-benzyl-2,6-piperazinedione

3-Phenyl-1-propylamine (3.63 g) and N-benzyliminodiacetic acid (6.0 g) was mixed and heated to 200° C. under a nitrogen atmosphere. The mixture was stirred at this temperature for 1 h, cooled and purified by column chromatography (SiO$_2$, 40°–60° C. petroleum ether/chloroform) to give the title material as a pale orange liquid (5.53 g, 64%).

EXAMPLE X2

1-(3-Phenylpropyl)-4-benzyl-2-hydroxy-6-oxopiperazine

Saturated aqueous sodium bicarbonate solution (20 ml) was added to a solution of 1-(3-phenylpropyl)-4-benzyl-2,6-piperazinedione (5.35 g) in ethanol (170 ml) at 5° C. and sodium borohydride (1.23 g) added portionwise to the resulting mixture at 5° C. over a period of 2 h. The mixture was stirred for a further 1 h at 5° C. and the solvent removed in vacuo. Water (50 ml) was added, and the mixture extracted with dichloromethane (3×50 ml), the extracts washed with brine and dried (MgSO$_4$). Evaporation of the solvent gave the title compound as a white solid (4.36 g, 81%)

EXAMPLE X3

2-Benzyl-4-oxo-1,2,3,4,6,7,8,12b-octahydropyrazino[2,1-a][2]benzazepine 1-(3-Phenylpropyl)-4-benzyl-2-hydroxy-6-oxopiperazine (2.6 g) and polyphosphoric acid (53 g) were mixed, heated at 180° C. and maintained at this temperature for ¾ h. The mixture was cooled to 60° C. and water (200 ml) added. The mixture was cooled, basified with sodium hydroxide solution, and extracted with chloroform (3×50 ml). The solvent was evaporated and the product crystallised from diethyl ether to give the title compound (0.78 g, 32%) m.p. 125°–8° C.

EXAMPLE X4

4-Oxo-1,2,3,4,6,7,8,12b-octahydropyrazino[2,1-a][2]-benzazepine

Hydrogenolysis of 2-benzyl-4-oxo-1,2,3,4,6,7,8,12b-octahydropyrazino[2,1-a][2]benzazepine (1.39 g) in solution in ethanol (40 ml) by treatment with hydrogen at 45° C. and atmospheric pressure in the presence of a palladium on charcoal catalyst (0.3 g) gave the title compound (0.6 g, 61%).

The following tabulated Examples 2 to 26 can be made in analogous fashion to the preparation of Example 1.

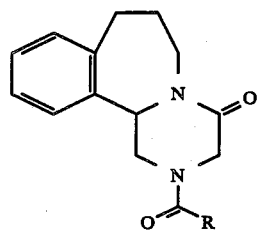

| Example No. | R | m.p. °C. | Calculated | | | | Found | | | |
|---|---|---|---|---|---|---|---|---|---|---|
| | | | C | H | N | Cl | C | H | N | Cl |
| 2 | ![phenyl] | 166–167 | Theoretical m/e 320.1525 | | | | Observed m/e 320.1538 | | | |
| 3 | ![4-OCH3-phenyl] | 167–171 | 71.98 | 6.33 | 7.99 | | 72.06 | 6.47 | 7.78 | |
| 4 | ![4-Cl-phenyl] | 184–186 | 67.70 | 5.40 | 7.89 | | 67.37 | 5.57 | 7.83 | |
| 5 | ![3-Cl-phenyl] | 148–151 | 67.70 | 5.40 | 7.89 | | 67.27 | 5.37 | 7.88 | |
| 6 | ![4-CH3-phenyl] | 179–181 | 75.42 | 6.63 | 8.38 | | 75.02 | 6.51 | 8.21 | |

-continued
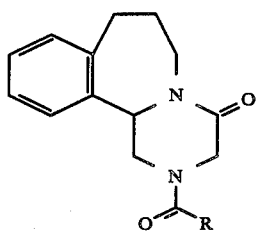
| Example No. | R | m.p. °C. | Microanalytical Data/Mass Spectral Data Calculated | | | Found | | |
|---|---|---|---|---|---|---|---|---|
| 7 | 3-methylphenyl | 152.5–153.0 | 75.42 | 6.63 | 8.38 | 75.72 | 6.67 | 8.38 |
| 8 | 2-methylphenyl | 127–128 | 75.42 | 6.63 | 8.38 | 75.42 | 6.67 | 8.34 |
| 9 | 4-nitrophenyl | 217–218 | 65.74 | 5.24 | 11.50 | 65.10 | 5.43 | 11.43 |
| 10 | 3-nitrophenyl | 170–171 | 65.74 | 5.24 | 11.50 | 65.54 | 5.03 | 11.43 |
| 11 | 4-aminophenyl·H₂O | 217–218 | 67.97 | 6.56 | 11.89 | 67.76 | 6.44 | 11.43 |
| 12 | 3-aminophenyl·H₂O | 98–101 | 67.97 | 6.56 | 11.89 | 67.79 | 6.35 | 11.68 |
| 13 | 4-(dimethylamino)phenyl | 197–198 | 72.70 | 6.93 | 11.56 | 72.46 | 6.95 | 11.37 |
| 14 | 4-hydroxyphenyl·½H₂O | 190–195 | 69.55 | 6.13 | 8.11 | 69.63 | 6.03 | 7.82 |
| 15 | 4-fluorophenyl | 168–169 | 70.99 | 5.66 | 8.28 | 70.33 | 5.62 | 8.12 |
| 16 | —CH₃ | 137–139 | 69.72 | 7.02 | 10.84 | 69.49 | 6.83 | 10.72 |
| 17 | —CH(CH₃)₂ | 162–163 | 71.30 | 7.74 | 9.78 | 71.18 | 7.87 | 9.73 |
| 18 | —C₅H₁₁(n) | 91–92 | 72.58 | 8.34 | 8.91 | 72.45 | 8.49 | 8.80 |

-continued

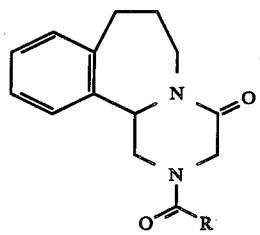

| Example No. | R | m.p. °C. | Microanalytical Data/Mass Spectral Data | | | | | | | |
|---|---|---|---|---|---|---|---|---|---|---|
| | | | Calculated | | | | Found | | | |
| 19 | cyclobutyl | 157–159 | 72.46 | 7.43 | 9.39 | | 72.51 | 7.55 | 9.06 | |
| | | | C | H | N | S | C | H | N | S |
| 20 | cyclopentyl | 154–155 | 73.03 | 7.74 | 8.97 | | 72.31 | 7.43 | 8.88 | |
| 21 | cycloheptyl | 160–165 | 74.08 | 8.29 | 8.23 | | 74.27 | 8.30 | 8.14 | |
| 22 | cyclohexenyl | 149–150 | 74.04 | 7.46 | 8.63 | | 73.97 | 7.46 | 8.61 | |
| 23 | cyclohexenyl | 183–185 | 74.04 | 7.46 | 8.63 | | 74.11 | 7.54 | 8.55 | |
| 24 | tetrahydropyranyl | 214–215 | Theoretical m/e 328.1787 | | | | Observed m/e 328.1795 | | | |
| 25 | thianyl | 164–165 | 66.25 | 7.02 | 8.13 | 9.31 | 66.49 | 7.05 | 8.09 | 8.98 |
| 26 | pyridyl | 170–171 | 71.01 | 5.96 | 13.07 | | 71.37 | 6.06 | 12.98 | |

EXAMPLE X5

2-(Triphenylmethyl)-4-oxo-1,2,3,4,6,7,8,12b-octahydropyrazino[2,1-a][2]benzazepine Triphenylmethyl chloride (0.47 g) was added to a mixture of 4-oxo-1,2,3,4,6,7,8,12b-octahydropyrazino[2,1-a][2]benzazepine (0.31 g) and triethylamine (0.25 ml) in chloroform (25 ml, ethanol-free) at 0°. The mixture was maintained at 0° for 30 min then at room temperature for 90 min. The solution was washed with saturated sodium bicarbonate solution, dried (MgSO₄) and evaporated. The residue was purified by column chromatography (SiO₂, Et₂O) to give the title compound (0.66 g, 100%) as a white powder.

EXAMPLE X6

4-Thioxo-1,2,3,4,6,7,8,12b-octahydopyrazino[2,1-a][2]benzazepine

A mixture of 2-(triphenylmethyl)-4-oxo-1,2,3,4,6,7,8,12b-octahydropyrazino-[2,1-a][2]benzazepine (0.66 g) and Lawesson's reagent (2,4-bis(4-methoxyphenyl)-1,3-dithia-2,4-diphosphetane-2,4-disulphide) (0.29 g) in HMPA (10 ml) was heated to 80° under a nitrogen atmosphere. The mixture was stirred at this temperature for 3 hr, cooled and partitioned between water and diethyl ether. The organic layer was washed with water and evaporated to a yellow foam. This residue was dissolved in acetone (20 ml), cooled to 0° and concentrated hydrochloric acid (0.5 ml) added. After stirring at room temperature for 30 min the mixture was evaporated and the residue partitioned between dilute hydrochloric acid and chloroform. The aqueous fraction was basified with sodium carbonate and extracted with chloroform. This chloroform fraction was washed with brine, dried ($K_2CO_3$) and evaporated to give the title compound as a white solid.

EXAMPLE 27

2-(Cyclohexylcarbonyl)-4-thioxo-1,2,3,4,6,7,8,12b-octahydropyrazino-[2,1-a][2]benzazepine Cyclohexanoyl chloride (0.16 g) was added to a mixture of 4-thioxo-1,2,3,4,6,7,8,12b-octahydropyrazino[2,1-a][2]benzazepin (0.24 g) and triethylamine (0.25 ml) in chloroform (20 ml, ethanol-free) at 0°. The mixture was maintained at 0° for 30 min then at room temperature for 5 hr. The solution was washed with, first, dilute hydrochloric acid, and secondly with sodium bicarbonate solution. The chloroform solution was dried ($MgSO_4$) and evaporated. The residue was purified by column chromatography ($SiO_2$, $Et_2O$) and recrystallised from dichloromethane/40°-60° C. petroleum ether to give white crystals of the title compound (55 mg, 16%) m.p. 150°-151° C.

Found: C: 70.4, H: 7.8, N: 8.1, S: 8.8%; $C_{20}H_{26}N_2OS$ requires: C: 70.1, H: 7.8, N: 8.2, S: 9.3%

EXAMPLE 28

2-(Cyclohexylcarbonyl)-4-thioxo-1,2,3,4,6,7,8,12b-octahydropyrazino-[2,1-a][2]benzazepine A mixture of 2-(cyclohexylcarbonyl)-4-oxo-1,2,3,4,6,7,8,12b-octahydropyrazino[2,1-a][2]benzazepine (0.30 g) and Lawesson's reagent (0.19 g) in HMPA (4 ml) was heated to 80° under a nitrogen atmosphere. The mixture was stirred at this temperature for 3 hr, coold and poured into water. This was extracted with diethyl ether. The organic layer was washed with water, dried ($MgSO_4$) and evaporated. The residue was purified by column chromatography ($SiO_2$, $Et_2O$) and recrystallisation ($CH_2Cl_2$/40-60 petroleum ether) to give white crystals of the title compounds (0.13 g, 41%) m.p. 150°-151° C.

By use of suitably substituted 3-phenylpropylamines in Examples X1 to X4, substituted 4-oxo-1,2,3,4,6,7,8,12b-octahydropyrazino[2,1-a][2]benzazepines were obtained which, on reaction with cyclohexanoyl chloride according to the procedure in Example 1, afforded the following substituted 2-(cyclohexylcarbonyl)-4-oxo-1,2,3,4,6,7,8,12b-octahydropyrazino[2,1-a][2]benzazepines:

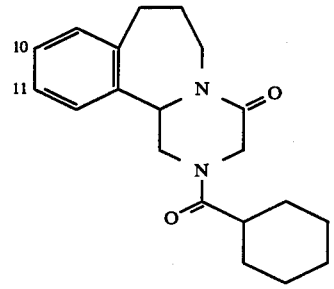

| Example | Substituent | Accurate Mass Measurement (m/e) Found | Calculated |
|---|---|---|---|
| 29 | 11-$CH_3$ | 340.2152 [$M^+$] | 340.2150 ($C_{21}H_{26}N_2O_2$) |
| 30 | 10,11-di$OCH_3$ | 386.2202 [$M^+$] | 386.2205 ($C_{22}H_{30}N_2O_4$) |

EXAMPLE 31

Nitration of 2-(cyclohexylcarbonyl)-4-oxo-1,2,3,4,6,7,8,12b-octahydropyrazino[2,1-a][2]benzazepine 2-(Cyclohexylcarbonyl)-4-oxo-1,2,3,4,6,7,8,12b-octahydropyrazino[2,1-a][2]benzazepine (600 mg, 1.8 mmol) was dissolved in concentrated sulphuric acid (7 ml) and concentrated nitric acid (4 ml) with cooling. The solution was heated at 35° C. for 2 hours, poured into water (100 ml) and extracted with $CHCl_3$ (2×50 ml). The combined extracts were dried ($MgSO_4$) and concentrated in vacuo to afford a mixture of the 10- and 11-mono-nitrated products which were separated by preparative HPLC [Ultrasil ODS 10μ, 25 cm×10 mm, MeOH:$H_2O$ (7:3), 1 ml/min].

Retention times 8.3 min and 9.2 min.

EXAMPLE X7

Resolution of 2H-4-oxo-1,2,3,4,6,7,8,12b-octahydropyrazino(2,1-a) (2) benzazepine (±) 2H-4-oxo-1,2,3,4,6,7,8,12b-octahyropyrazino (2,1-a) (2) benzazepine (3.2 g, 0.0148 mol) was dissolved in methanol (35 ml) and a solution of (−) tartaric acid (2.45 g, 0.0163 mol) in methanol (140 ml) added.

The mixture was heated on a steam bath, filtered whilst hot, and allowed to cool. White crystals were deposited, and these were filtered, and recrystalised from methanol (250 ml) to give the (−) tartarate salt of (−) 2H-4-oxo-1,2,3,4,6,7,8,12b-octahydropyrazino (2,1-a) (2) benzazepine $(α)_D^{22}$ −149° ($H_2O$).

A solution of this salt in water gave, upon basification with ammonium hydroxide and extraction with chloroform, the free base (−) 2H-4-oxo-1,2,3,4,6,7,8,12b-octahydropyrazino (2,1-a) (2) benzazepine as a white solid $(α)_D^{22}$ −221° ($CH_3OH$).

Similarly, using (+) tartaric acid in place of (−) tartaric acid was obtained:

(+) 2H-4-oxo-1,2,3,4,6,7,8,12b-octahydropyrazino (2,1-a) (2) benzazepine (+) tartrate $(α)_D^{22}$ +153° ($H_2O$). Found C; 55.7, H; 6.1, N; 7.4%. $C_{17}H_{22}N_2O_7$ requires C; 55.7, H; 6.0, N; 7.6% and (+) 2H-4-oxo-1,2,3,4,6,7,8,12b-octahydropyrazino (2,1-a) (2) benzazepine free base $(α)_D^{22}$ +212° ($CH_3OH$).

EXAMPLE 32

(λ)

2-(cyclohexylcarbonyl)-4-oxo-1,2,3,4,6,7,8,12b-octahydropyrazino (2,1-a) (2) benzazepine The title compound was obtained by the method of example I using (+) 2H-4-oxo-1,2,3,4,6,7,8,12b-octahydropyrazino (2,1-a) (2) benzazepine in place of the racemic amine. The product was purified by column chromatography (Si/CHCl$_3$). $(\alpha)_D^{22}$ +41° (CH$_3$OH).

EXAMPLE 33

(−)

2-(cyclohexylcarbonyl)-4-oxo-1,2,3,4,6,7,8,12b-octahydropyrazino (2,1-a) (2) benzazepine The title compound was obtained as a white solid by the procedure outlined in example I using (−) 2H-4-oxo-1,2,3,4,6,7,8,12b-octahydropyrazino (2,1-a) (2) benzazepine in place of the racemic amine. The product was purified by column chromatography (Si/CHCl$_3$). $(\alpha)_D^{22}$ −42° (CH$_3$OH).

EXAMPLE 34

2-(Cyclohexylthiocarbonyl)-4-oxo-1,2,3,4,6,7,8,12b-octahydropyrazino-[2,1-a][2]benzazepine Methyl cyclohexanecarbodithioate (0.24 g) was added to a solution of 4-oxo-1,2,3,4,6,7,8,12b-octahydropyrazino[2,1-a][2]benzazepine (0.3 g) in dimethylformamide (5 ml). The mixture was refluxed for 4 h, cooled and poured into water. This was extracted with diethyl ether; the ether solution was dried (MgSO$_4$) and evaporated. The residue was purified by column chromatography (SiO$_2$, diethyl ether). m/e observed: 342.1770 C$_{20}$H$_{26}$N$_2$OS requires 342.1766

EXAMPLE 35

2-(Cyclohexylcarbonyl)-4-oxo-1,2,3,6,7,12b-hexahydropyrazino[1,2-d][1,4]benzoxazepine 4-Oxo-1,2,3,6,7,12b-hexahydropyrazino[1,2-d][1,4]benzoxazepine (0.9 g) and triethylamine (1 g) were dissolved in dichloromethane (20 ml), cooled in ice and cyclohexanoyl chloride (0.7 g, 1.1 equiv.) added. The mixture was stirred at room temperature for 3 h, then washed with dilute aqueous hydrochloric acid, followed by dilute aqueous ammonia solution. Evaporation of the dichloromethane gave an oil which was purified by column chromatography (SiO$_2$/chloroform) and crystallised from ether/40°-60° petroleum ether to give white crystals of the title compound m.p. 92°-3°;

found: C, 69.53; H, 7.40; N, 8.54% C$_{19}$H$_{24}$N$_2$O$_3$ requires C, 69.49; H, 7.37; N, 8.53%.

EXAMPLE X8

1-(2-Phenoxyethyl)-4-benzyl-2,6-piperazinedione

2-Phenoxyethylamine (1.37 g) and N-benzyliminodiacetic acid (2.23 g) were mixed and heated to 225°, and maintained at this temperature for 15 min. After cooling, chloroform was added and the product purified by column chromatography (SiO$_2$/CHCl$_3$) to give the title compound as a reddish oil (2.1 g).

EXAMPLE X9

1-(2-Phenoxyethyl)-4-benzyl-2-hydroxy-6-oxopiperazine 1-(2-Phenoxyethyl)-4-benzyl-2,6-piperazinedione (2.24 g) in ethanol (60 ml) and saturated sodium bicarbonate solution (15 ml) was cooled to 5° and sodium borohydride (0.4 g) added. The mixture was stirred at 5° for 1 h, water (150 ml) added and the mixture extracted with chloroform (3×75 ml). Evaporation of the chloroform gave the title compound as an off-white solid (2.1 g).

EXAMPLE X10

2-Benzyl-4-oxo-1,2,3,6,7,12b-hexahydropyrazino[1,2-d][1,4]benzoxazepine 1-(2-Phenoxyethyl)-4-benzyl-2-hydroxy-6-oxopiperazine (4 g) was added to concentrated sulphuric acid (50 ml) at 0°-10° and the mixture stirred for 30 min. The resulting solution was poured onto ice, basified with NH$_4$OH and extracted with chloroform to give the title compound as a pale oil (2 g).

EXAMPLE X11

4-Oxo-1,2,3,6,7,12b-hexahydropyrazino[1,2-d][1,4]-benzoxazepine

Hydrogenation of 2-benzyl-4-oxo-1,2,3,6,7,12b-hexahydropyrazino[1,2-d][1,4]benzoxazepine in 90% acetic acid over a palladium on charcoal catalyst (5%) at 50° C. and a pressure of 400KN$_m^{-2}$ of hydrogen gave, after basification and extraction, the title compound.

PHARMACOLOGICAL DATA

A cat infected with *Taenia taeniaeformis* and *Dipylidium caninum* was treated with 2-(cyclohexylcarbonyl)-4-oxo-1,2,3,4,6,7,8,12b-octahydropyrazino-[2,1-a][2]benzazepine at 30 mg/kg p.o. This treatment completely removed the tapeworm infections.

The following compounds were administered orally to cats infected with *Dipylidium caninum* and/or *Taenia taeniaeformis* and the following activities noted.

| Compound of Example No. | Dose mg/kg p.o. | Activity % Taenia | Activity % Dipylidium |
| --- | --- | --- | --- |
| 1 | 1 | 100 | 100 |
| 20 | 1 | 100 | 100 |
| 21 | 5 | 100 | NI |
| 22 | 5 | 100 | NI |
| 35 | 5 | 100 | 100 |

NI = Not infected

We claim:
1. A compound of formula (I):

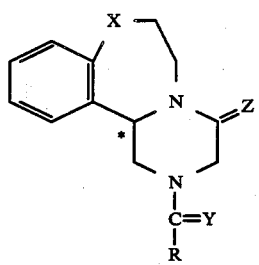

in which R is phenyl or phenyl substituted with at least one moiety selected from halogen, $C_{1-6}$ alkyl, $C_{1-6}$ alkoxy, nitro, amino, mono-or-di-$C_{1-6}$ alkylamino, and hydroxy; $C_{3-8}$ cycloalkyl; $C_{5-8}$ cycloalkenyl; $C_{1-8}$ alkyl which may be straight or branched; $C_{2-8}$ alkenyl which may be straight or branched; 5- or 6-membered saturated or unsaturated cyclic ring having one or more heteroatoms selected from oxygen, sulphur and nitrogen; or phenyl $C_{1-4}$ alkyl or phenyl $C_{1-4}$ alkyl wherein the phenyl is substituted with at least one moiety selected from halogen, $C_{1-6}$ alkyl; $C_{1-6}$ alkoxy, nitro, amino, mono-or-di-$C_{1-6}$ alkylamino, and hydroxy, each of Y and Z, which may be the same or different, is oxygen or sulphur and X is —$CH_2$ or oxygen.

2. A method of treatment and prophylaxis of helminth infections in a human or in a domestic or farm animal comprising administering to said human or domestic or farm animal an effective non-toxic amount of a compound of the formula (I):

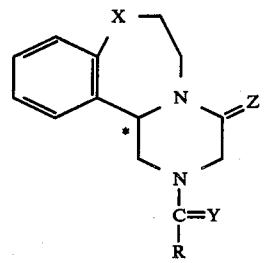

in which R is phenyl; or phenyl substituted with at least one moiety selected from halogen, $C_{1-6}$ alkyl, $C_{1-6}$ alkoxy, nitro, amino, mono-or-di-$C_{1-6}$ alkylamino, and hydroxy; $C_{3-8}$ cycloalkyl; $C_{5-8}$ cycloalkenyl; $C_{1-8}$ alkyl which may be straight or branched; $C_{2-8}$ alkenyl which may be straight or branched; 5- or 6-membered saturated or unsaturated cyclic ring having one or more hetero-atoms selected from oxygen, sulphur and nitrogen; or phenyl $C_{1-4}$ alkyl, or phenyl $C_{1-4}$ alkyl wherein the phenyl is substituted with at least one moiety selected from halogen, $C_{1-6}$ alkyl, $C_{1-6}$ alkoxy, nitro, amino, mono-or-di-$C_{1-6}$ alkylamino, and hydroxy; and each of Y and Z, which may be the same or different, is oxygen or sulphur; and X is —$CH_2$ or oxygen.

3. The method of claim 2 wherein said helminth infections are tapeworm infections.

* * * * *

UNITED STATES PATENT AND TRADEMARK OFFICE
CERTIFICATE OF CORRECTION

PATENT NO.   :   4,866,056
DATED        :   September 12, 1989
INVENTOR(S)  :   Roderick J. Dorgan et al It is certified that error appears in the above-identified patent and that said Letters Patent is hereby corrected as shown below:

Insert on the face of the patent to read after item [2]

--[30] Foreign Application Priority Data

July 16, 1983 [G.B] United Kingdom---8319357

December 24, 1983 [G.B.] United Kingdom---8334502--

Signed and Sealed this

Eleventh Day of September, 1990

*Attest:*

HARRY F. MANBECK, JR.

*Attesting Officer*　　　*Commissioner of Patents and Trademarks*